(12) United States Patent
Williams

(10) Patent No.: US 11,090,114 B2
(45) Date of Patent: *Aug. 17, 2021

(54) SYSTEM AND METHOD FOR MONITORING TISSUE TEMPERATURE

(71) Applicant: Gyrus Medical Limited, Cardiff (GB)

(72) Inventor: David Nicholas Williams, Caerphilly (GB)

(73) Assignee: Gyrus Medical Limited, Cardiff (GB)

( * ) Notice: Subject to any disclaimer, the term of this patent is extended or adjusted under 35 U.S.C. 154(b) by 462 days.

This patent is subject to a terminal disclaimer.

(21) Appl. No.: 15/597,883

(22) Filed: May 17, 2017

(65) Prior Publication Data

US 2018/0008346 A1 Jan. 11, 2018

(30) Foreign Application Priority Data

Jul. 11, 2016 (GB) ..................................... 1612001

(51) Int. Cl.
*A61B 18/04* (2006.01)
*A61B 18/18* (2006.01)
*A61B 18/00* (2006.01)

(52) U.S. Cl.
CPC ..................... *A61B 18/1815* (2013.01); *A61B 2018/00023* (2013.01); *A61B 2018/00101* (2013.01); *A61B 2018/00577* (2013.01); *A61B 2018/00642* (2013.01); *A61B 2018/00678* (2013.01); *A61B 2018/00708* (2013.01); *A61B 2018/00821* (2013.01); *A61B 2018/00892* (2013.01); *A61B 2018/1823* (2013.01); *A61B 2018/1838* (2013.01); *A61B 2018/1861* (2013.01); *A61B 2018/1869* (2013.01)

(58) Field of Classification Search
CPC ...... A61B 18/1815; A61B 2018/00577; A61B 2018/00714; A61B 2018/00821; A61B 2018/1823
See application file for complete search history.

(56) References Cited

U.S. PATENT DOCUMENTS

| 6,245,065 | B1 | 6/2001 | Panescu et al. | |
|---|---|---|---|---|
| 8,764,744 | B2 * | 7/2014 | Brannan | A61B 18/18 606/41 |
| 2005/0288662 | A1 * | 12/2005 | Uchida | A61B 18/1206 606/34 |
| 2007/0066972 | A1 * | 3/2007 | Ormsby | A61B 18/1492 606/41 |
| 2009/0192507 | A1 * | 7/2009 | Luttich | A61B 18/1477 606/41 |
| 2011/0306969 | A1 * | 12/2011 | Coe | A61B 18/1815 606/41 |

(Continued)

FOREIGN PATENT DOCUMENTS

EP 2497437 A1 9/2012

OTHER PUBLICATIONS

Styles-Davis, E., "UK Search Report", prepared for application No. 1612001.6, Jan. 3, 2017, 5 pages.

*Primary Examiner* — Jaymi E Della
(74) *Attorney, Agent, or Firm* — Winstead PC

(57) ABSTRACT

A method and system for monitoring tissue temperature during microwave ablation of such tissue is disclosed. The method includes applying a predetermined correction value to a temperature measurement to provide a corrected temperature value.

15 Claims, 5 Drawing Sheets

(56) References Cited

U.S. PATENT DOCUMENTS

| | | |
|---|---|---|
| 2012/0323227 A1 | 12/2012 | Wolf et al. |
| 2014/0188107 A1 | 7/2014 | Weber |
| 2015/0105765 A1* | 4/2015 | Panescu ................ A61B 18/02 606/34 |
| 2016/0184013 A1 | 6/2016 | Brannan et al. |
| 2016/0324575 A1* | 11/2016 | Panescu ............... A61B 5/0422 |

* cited by examiner

SYSTEM AND METHOD FOR MONITORING TISSUE TEMPERATURE

FIELD OF THE INVENTION

The present invention relates to systems and methods for monitoring tissue temperature, particularly during microwave ablation of such tissue.

BACKGROUND OF THE INVENTION

In the treatment of tumours, for example tumours caused by a disease such as cancer, it is known to use microwave ablation techniques to ablate the tumour. Such microwave ablation techniques typically ablate the targeted tissue by delivering a controlled amount of microwave energy into the tumour.

Minimally-Invasive techniques for delivering such microwave energy have been shown to be effective in the treatment of tumours. In a minimally-invasive technique, a microwave emitter is inserted directly into a point of treatment, either using a normal body orifice or via percutaneous insertion. Such minimally-invasive procedures and devices provide a means of treating tumours in patients who either cannot undergo other forms of treatment (e.g. radiotherapy, surgical resection, chemotherapy) or where ablation is preferred as a therapy.

One example type of commonly used microwave antenna assembly includes a dipole antenna, which consists of a coaxial construction having an inner conductor and an outer conductor with a dielectric junction (feed point) separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction.

Careful monitoring of the temperature of the tissue surrounding the tumour can significantly improve the outcome of ablation treatment. Existing designs of microwave ablation apparatus make use of thermocouples or other temperature sensors mounted on the probe; they can be used to estimate the progress of the ablated region. However, the measurement of temperature of the tumour and or the surrounding healthy tissue of the treatment region can be improved.

SUMMARY OF THE INVENTION

According to a first aspect of the present invention, there is provided a method of monitoring tissue temperature during microwave ablation of such tissue, the method comprising providing a power source operable to provide a controlled microwave energy output, providing a microwave probe having a body and an antenna extending through the body and operable to deliver microwave energy from the power source out of the microwave probe, providing a thermocouple on the body of the microwave probe, the thermocouple being separated from the body by a layer of thermally insulating material, the thermocouple being operable to generate an output voltage in dependence upon a temperature experienced by the thermocouple, supplying a controlled microwave energy output from the power source to the antenna, thereby causing microwave energy to radiate from the antenna to form an ablation zone, detecting an output voltage generated by the thermocouple in response to a temperature experienced by the thermocouple, determining a temperature value relating to the detected output voltage, and applying a predetermined correction value to the determined temperature value, so as to provide a corrected temperature value.

According to a second aspect of the present invention, there is provided a method of controlling a microwave probe during microwave ablation of tissue, the method comprising a method of monitoring tissue temperature according to the first aspect, and further comprising controlling the microwave energy supplied from the power source to the antenna such that the corrected temperature value reaches a predetermined target value.

According to a third aspect of the present invention, there is provided a microwave ablation apparatus comprising a power source operable to provide a controlled microwave energy output, a microwave probe having a body and an antenna extending through the body and operable to deliver microwave energy from the power source out of the microwave probe, a thermocouple on the body of the microwave probe, the thermocouple being separated from the body by a layer of thermally insulating material, the thermocouple being operable to generate an output voltage in dependence upon a temperature experienced by the thermocouple, a detector operable to detect an output voltage generated by the thermocouple in response to a temperature experienced by the thermocouple, a calculation unit operable to determine a temperature value relating to the detected output voltage, a correction unit operable to apply a predetermined correction value to such a determined temperature value, and to provide a corrected temperature value, and a controller operable to control microwave energy supplied to the antenna from the power source such that the corrected temperature value reaches a predetermined target value.

In one example, the predetermined correction value relates to the location of the thermocouple on the body of the microwave probe.

In one example, the predetermined correction value relates to time of application of the microwave energy.

In one example, the predetermined correction value relates to a temperature of a coolant fluid used inside the body of the microwave probe.

In one example, the corrected temperature value is a predetermined multiple of the determined temperature value.

In one example, the predetermined correction value is chosen from a range of predetermined correction values in dependence upon power level and application time of the microwave energy.

In one example, a plurality of such thermocouples are provided on the body of the microwave probe, the thermocouples being located at respective locations on the body, and a respective corrected temperature value is provided for each thermocouple, in dependence upon respective determined temperature values and correction values for each thermocouple.

In one example, the supply of microwave energy from the power source is terminated when the corrected temperature value substantially reaches the predetermined target value.

DETAILED DESCRIPTION OF THE PREFERRED EMBODIMENTS

Figure 1:
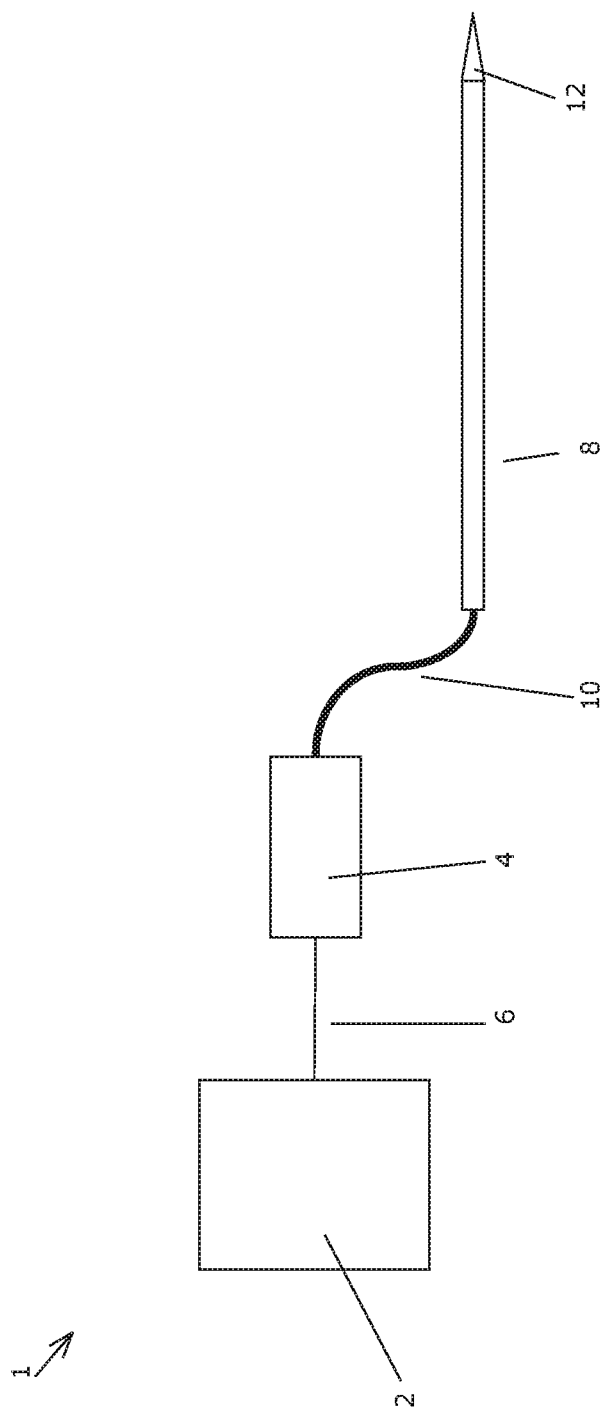
FIG. 1 illustrates of a microwave ablation apparatus.

FIG. 1 is a schematic diagram illustrating a microwave ablation system 1 comprising a controller unit 2, and a microwave power generator 4 which is connected to the controller via a control connection 6. An ablation antenna assembly 8 is connected to the microwave power generator 4 via a power connection 10. The antenna assembly includes a tip portion 12 which aids insertion of the antenna assembly into the tissue being treated, and enables a desired output pattern of microwave energy from the antenna assembly 8. The controller unit 2 is operable to control the power generator 4 to supply the correct magnitude and frequency of microwave energy to the antenna assembly 8. For example, the microwave energy may be delivered using the 911 MHz, or 2.45 GHz wavebands, or any suitable waveband up to 14 GHz.

Figure 2:
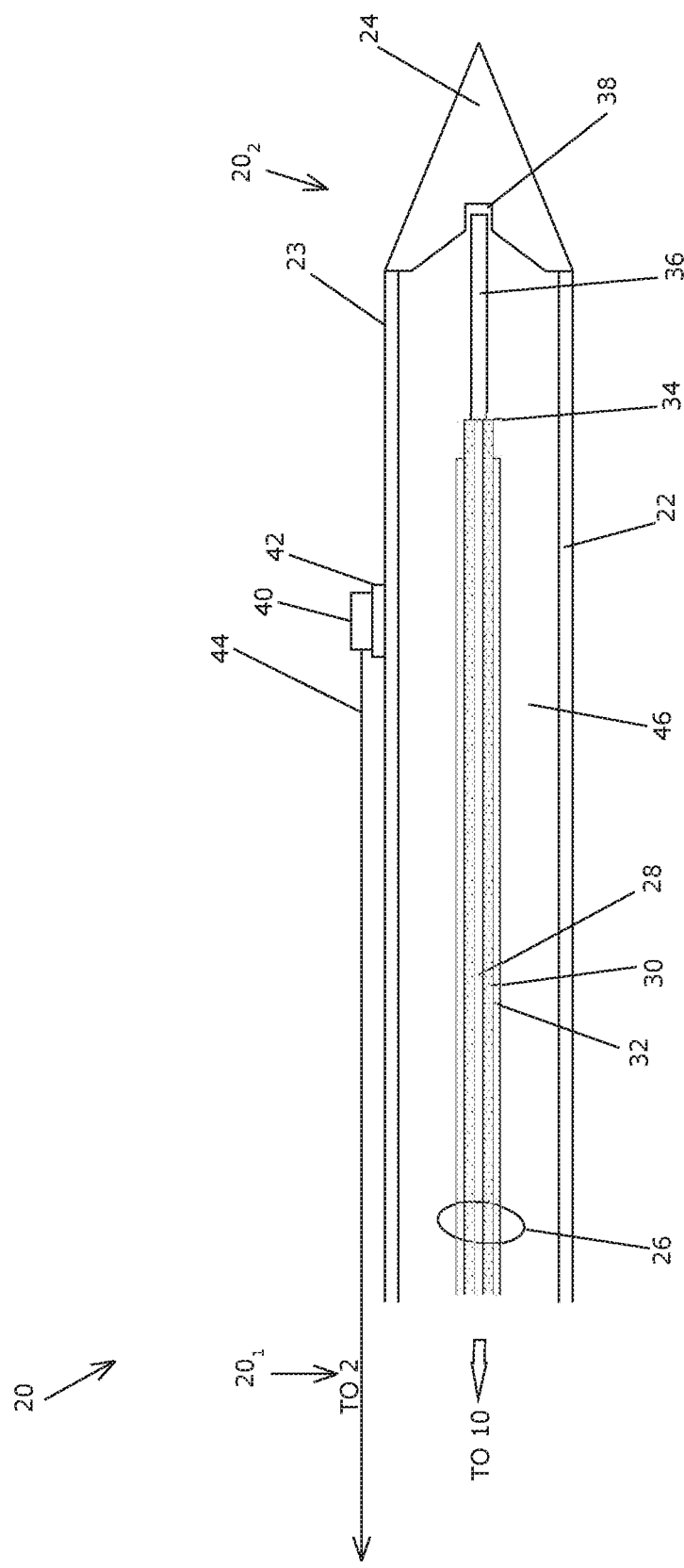
FIG. 2 illustrates a microwave probe of the apparatus of FIG. 1.

FIG. 2 is a cross-sectional view of part of an exemplary microwave probe assembly 20 embodying an aspect of the present invention. It will be readily appreciated that other constructions of probe assembly may embody aspects of the present invention. The microwave probe assembly 20 comprises a body 22, which is preferably cylindrical in form. The body 22 extends from a first (proximal) end $20_1$ to a second (distal) end $20_2$, and defines a longitudinal axis of the assembly. The body 22 defines an inner volume, in which most of the other components of the assembly are housed. The body 22 provides the assembly with the necessary rigidity for insertion into the tissue being treated. The body 22 is preferably of a rigid material, such as a composite material (for example glass fibre, carbon fibre, aramid fibre), stainless steel, other biocompatible metals (e.g. titanium) or combinations of, and is typically 1.5 to 3 mm mm in diameter.

An applicator tip 24 is attached to the second end $20_2$ of the body, to close off the inner volume at the second end. The applicator tip is preferably a faceted trocar and has a relatively sharp distal end point. The applicator tip 24 is designed to be suitable for insertion into the tissue being treated, and partly to affect the transmission pattern for microwave energy into that tissue. It also forms a water tight seal to the internal volume of the body 22, if required when the applicator uses an internal cooling fluid.

A coaxial conductor assembly 26 extends along the inner volume of the body 22 from the first end $20_1$ towards the second end $20_2$. The coaxial conductor assembly 26 is connectable, at a proximal end thereof, to the microwave energy generator 4 of FIG. 1. The coaxial conductor assembly 26 extends substantially along the longitudinal axis of the body 22, and comprises an inner conductor 28. The inner conductor 28 is of an electrically conductive material such as copper. Surrounding the inner conductor 28 is a dielectric layer 30 which extends along the inner conductor 28, radially outwardly thereof. The dielectric layer 30 is of any appropriate dielectric material. Surrounding the dielectric layer 30, is an outer conductor 32, which is of an electrically conductive material such as copper. The outer conductor 32 extends along the dielectric layer 30, radially outwardly thereof. Typically, the inner conductor 28 is a wire having a circular cross section, such that the dielectric layer 30 is a cylinder of dielectric material surrounding an outer surface of the inner conductor 28. The outer conductor 32 is then formed by a cylinder of electrically conductive material surrounding an outer surface of the dielectric layer 30.

The inner conductor 28 defines a signal feed-point 34 at its distal end (that is, the end towards the second end $20_2$ of the body 22). A dipole tip portion 36 extends longitudinally from the distal end of the coaxial conductor assembly 36 into a reception aperture in the applicator tip 24. The reception aperture 38 is located centrally with respect to the longitudinal axis of the assembly within the applicator tip 24. The reception aperture 38 is designed so as to locate centrally the dipole tip portion 36 into the tip 24. The tip material is chosen for it mechanical and electrical properties, which have to be considered in the design.

The dielectric layer 30 extends along the complete length of the inner conductor 28 to the distal end thereof adjacent the dipole tip portion 36. The outer conductor 32 stops short of the distal end of the inner conductor 28 and dielectric layer 32, and so is spaced apart longitudinally from the signal feed-point 34 and dipole tip portion 36.

In one example constructions, a dielectric fluid 46 may be provided within the inner volume of the body 20 in order to provide a key functional element to the microwave design and also provide a cooling fluid for the antenna assembly. This fluid will typically be isotonic saline or deionised water.

In a first embodiment of an aspect of the present invention, a first thermocouple 40 is located on an outer surface 23 of the body 22. The first thermocouple 40 is not shown to scale in FIG. 2, but has been enlarged in order to show the details of the embodiment. The exact position of the first thermocouple 40 on the outer surface 23 of the body 22 is chosen in order to provide the most appropriate temperature readings, as will be discussed below.

A first layer 42 of thermally insulating material is provided between the first thermocouple 40 and the outer surface 23 of the body 22. This first layer 42 serves to insulate the first thermocouple 40 from the heat of the body 22, and so aids more accurate measurement of temperature outside of the body 22. This accuracy is improved by virtue of insulating the first thermocouple 40 from the temperature of the body 22 and from the effects of the cooling fluid 46 used within the body 22.

The first thermocouple 40 is connected to the controller 2 of FIG. 1 by a signal connection 44. The signal connection 44 transfers the output of the first thermocouple 40 to the controller 2. As is well known, the output of a thermocouple is a voltage, the magnitude of which is dependent upon the temperature being experienced by the thermocouple. In the present case, the first thermocouple 40 supplies a first output signal, via the signal connection 44, to the controller 2. The first output signal relates to the temperature outside of the body 22, with reduced effect of the temperature within the body 22. As will be described below, the controller 2 receives and processes the first output signal.

Figure 3:
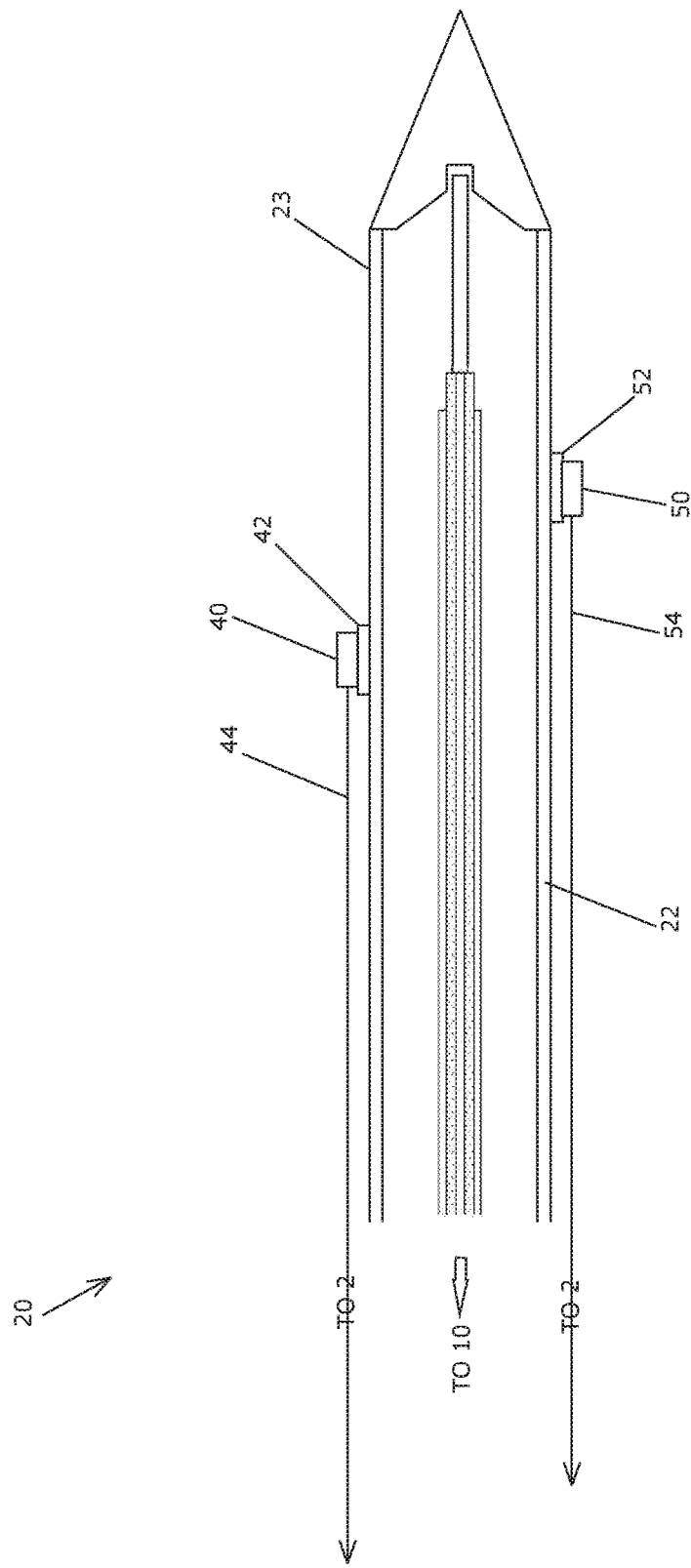
FIG. 3 illustrates an alternative microwave probe of the apparatus of FIG. 1.

A second embodiment of an aspect of the present invention is illustrated in FIG. 3, which shows a microwave probe of the same basic structure to that of the embodiment of FIG. 2. The microwave probe 20 of FIG. 3 differs from that of FIG. 2 by virtue of the provision of a second thermocouple 50 in addition to the first thermocouple 40 of FIG. 2. The second thermocouple 50 is provided at position on the outer surface 23 of the body 22 of the probe 20 different to that of the first thermocouple 40. The relative positions of the first and second thermocouples are chosen so as to provide the lost useful temperature measurements relating to the tissue being ablated.

A second layer 52 of thermally insulating material is provided between the second thermocouple 50 and the outer surface 23 of the body 22. This second layer 52 serves to insulate the second thermocouple 50 from the heat of the body 22, and so aids more accurate measurement of temperature outside of the body 22. This accuracy is improved by virtue of insulating the second thermocouple 50 from the temperature of the body 22 and from the effects of the cooling fluid 46 used within the body 22.

The second thermocouple 50 is connected to the controller 2 of FIG. 1 by a signal connection 54. The signal connection 54 transfers the output of the thermocouple 40 to the controller 2. In the present case, the second thermocouple 50 supplies a second output signal, via the signal connection 54, to the controller 2. The second output signal relates to the temperature outside of the body 22, with reduced effect of the temperature within the body 22. As will be described below, the controller 2 receives and processes the second thermocouple output signal.

Figure 4:
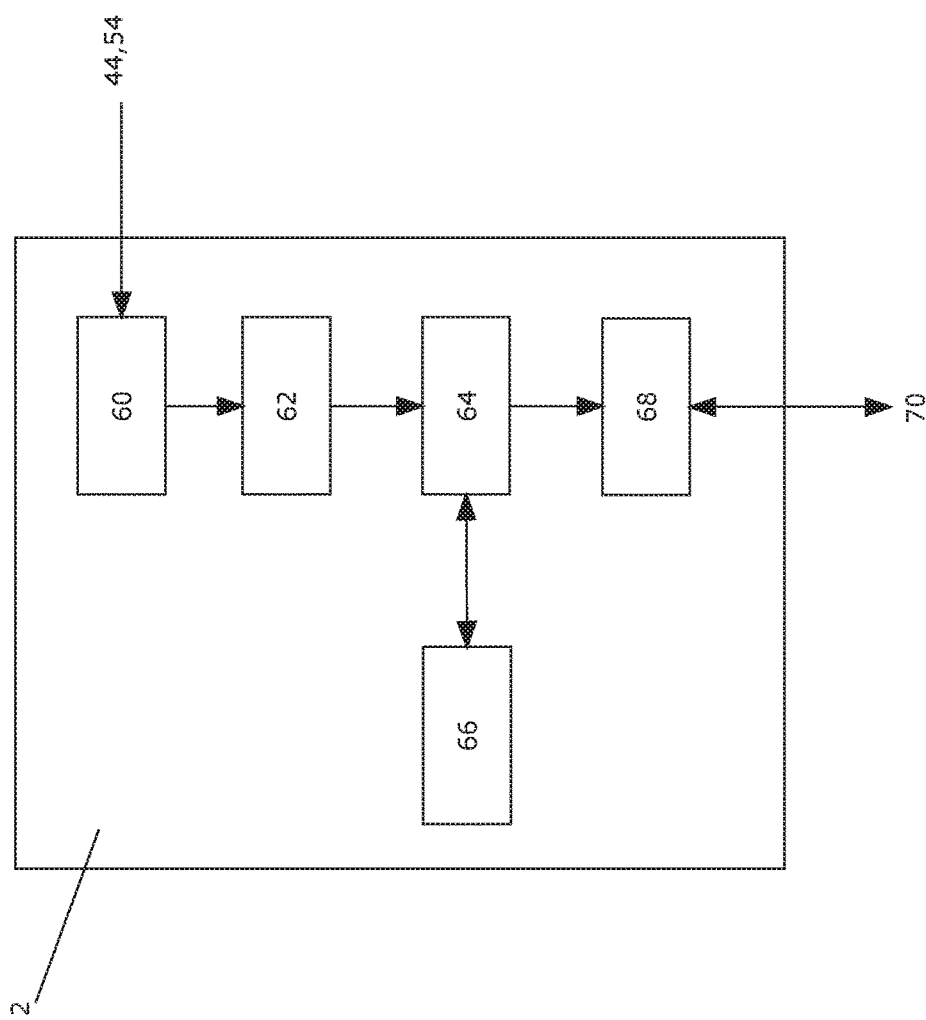
FIG. 4 illustrates a controller of the apparatus of FIG. 1.
Figure 5:
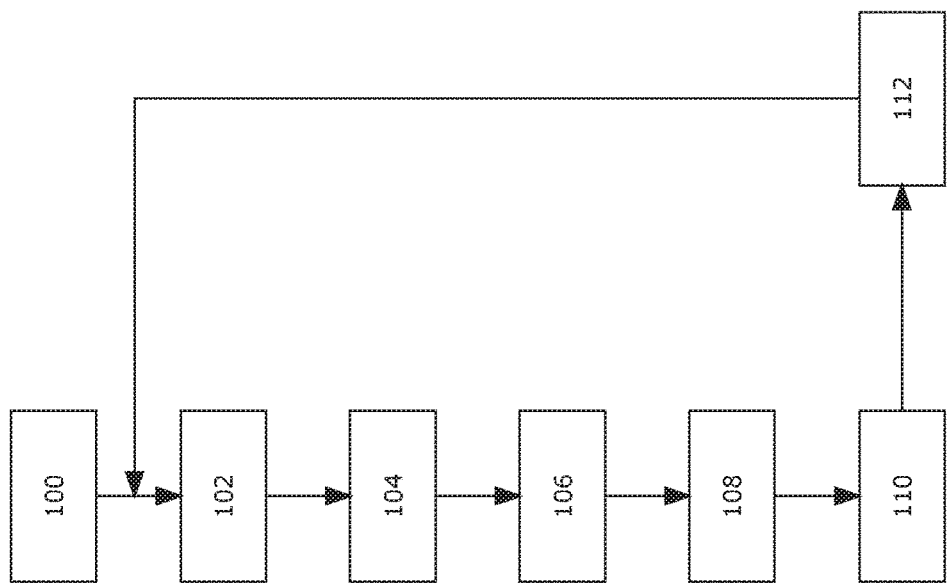
FIG. 5 is a flowchart illustrating a method of use of the apparatus of FIG. 1.

FIG. 4 illustrates schematically the controller 2 of FIG. 1, and FIG. 5 illustrates operation of the system using such a controller. The first step (100) is to provide the power supply, controller, and microwave probe assembly. Microwave energy is then supplied (102) to the microwave probe.

The controller 2 comprises a detector 60 connected to receive the first output signal from the first thermocouple 40, and the second output signal from the second thermocouple 50, if provided. The detector 60 is operable to receive (step 104) the output signal(s) and provide (step 106) a detected output signal as an output to a calculation unit 62.

The calculation unit 62 is operable to determine (step 108) a temperature value that corresponds to each received detected output signal. The calculated temperature value is then provided to a correction unit 64 which is operable to apply (step 110) a predetermined correction factor to received calculated temperature values in order to provide a more accurate measurement of temperature of the zone being ablated outside of the microwave probe assembly.

The correction unit 64 operates to apply a mathematical correction factor to the calculated temperature values. The correction factor may be a simple multiple factor, to give a multiple of the calculated temperature value as the corrected value. An alternative correction factor may be based on time of application of microwave energy, or of the temperature of the coolant used in the probe assembly. Other bases for the correction factor may include one or more of the following considerations: the nature of the tumour i.e. the primary cancer type, the host organ, the patient's physical condition (e.g. blood flow, body temperature etc), previous medical cases derived from a user database.

These correction factors may be used singly, or in an appropriate combination. Respective correction factors are provided for each thermocouple used in the probe, and are preferably characterised for different microwave power levels and application times. The correction factors are stored in a data storage unit 66 accessible by the correction unit 64. The correction factors are preferably determined using experimental data obtained using comparison of thermocouple signals with measurements from other devices, such as fluoroptic probes, measuring the temperature of tissue during experimental ablation processes. The correction factors may be updated during operation of the system.

The calculated temperature values are provided to a control unit 68 which is operable to control (step 112) supply of microwave energy to the microwave probe assembly by supplying control signals to the power supply via a control connection 70. The control unit 68 controls the microwave power supply on the basis of the corrected temperature value. When a desired corrected temperature value is reached, the control unit operates to turn off the supply of microwave energy in order to stop the ablation process.

The control unit is operable to determine an appropriate end point for the application of microwave energy to the tissue being ablated on the basis of the corrected temperature values. Such accurate determination of the temperature of the ablated tissue as treatment proceeds leads to more accurate and successful treatment by ablation of the appropriate tissue.

What is claimed is:

1. A method of monitoring tissue temperature during microwave ablation of such tissue, the method comprising:
   providing a power source operable to provide a controlled microwave energy output;
   providing a microwave probe having a body and an antenna extending through the body and operable to deliver the microwave energy from the power source out of the microwave probe;
   providing a thermocouple on an outer surface of the body of the microwave probe, the thermocouple being separated from the body by a layer of thermally insulating material, the thermocouple being operable to generate an output voltage in dependence upon a temperature experienced by the thermocouple;
   supplying the controlled microwave energy output from the power source to the antenna, thereby causing the microwave energy to radiate from the antenna to form an ablation zone;
   detecting an output voltage generated by the thermocouple in response to the temperature experienced by the thermocouple;
   determining a temperature value relating to the detected output voltage;
   applying a predetermined correction value to the determined temperature value so as to provide a corrected temperature value; and
   wherein the predetermined correction value relates to a temperature of a coolant fluid used inside the body of the microwave probe.

2. The method as claimed in claim 1, wherein the predetermined correction value relates to a location of the thermocouple on the body of the microwave probe.

3. The method as claimed in claim 1, wherein the predetermined correction value relates to time of application of the microwave energy.

4. The method as claimed in claim 1, wherein the corrected temperature value is a predetermined multiple of the determined temperature value.

5. The method as claimed in claim 1, wherein the predetermined correction value is chosen from a range of predetermined correction values in dependence upon power level and application time of the microwave energy.

6. The method as claimed in claim 1, wherein the thermocouple comprises a plurality of thermocouples on the body of the microwave probe, the plurality of thermocouples being located at respective locations on the body, and wherein a respective corrected temperature value is provided for each of the plurality of thermocouples, in dependence upon respective determined temperature values and predetermined correction values for each of the plurality of thermocouples.

7. The method of controlling the microwave probe during the microwave ablation of the tissue method comprising the method of monitoring the tissue temperature as claimed in claim 1, and further comprising controlling the microwave energy supplied from the power source to the antenna such that the corrected temperature value substantially reaches a predetermined target value.

8. The method as claimed in claim 7, further comprising terminating the supply of the microwave energy from the power source when the corrected temperature value substantially reaches the predetermined target value.

9. A microwave ablation apparatus comprising:
a power source operable to provide a controlled microwave energy output;
a microwave probe having a body and an antenna extending through the body and operable to deliver the microwave energy from the power source out of the microwave probe;
a thermocouple on an outer surface of the body of the microwave probe, the thermocouple being separated from the body by a layer of thermally insulating material, the thermocouple being operable to generate an output voltage in dependence upon a temperature experienced by the thermocouple;
a detector operable to detect an output voltage generated by the thermocouple in response to the temperature experienced by the thermocouple;
a calculation unit operable to determine a temperature value relating to the detected output voltage;
a correction unit operable to apply a predetermined correction value to the determined temperature value, and to provide a corrected temperature value;
a controller operable to control the microwave energy supplied to the antenna from the power source such that the corrected temperature value reaches a predetermined target value; and
wherein the predetermined correction value relates to a temperature of a coolant fluid used inside the body of the microwave probe.

10. The apparatus as claimed in claim 9, wherein the predetermined correction value relates to a location of the thermocouple on the body of the microwave probe.

11. The apparatus as claimed in claim 9, wherein the predetermined correction value relates to time of application of the microwave energy.

12. The apparatus as claimed in claim 9, wherein the corrected temperature value is a predetermined multiple of the determined temperature value.

13. The apparatus as claimed in claim 9, wherein the predetermined correction value is chosen from a range of predetermined correction values in dependence upon power level and application time of the microwave energy.

14. The apparatus as claimed in claim 9, wherein the thermocouple comprises a plurality of thermocouples on the body of the microwave probe, the plurality of thermocouples being located at respective locations on the body, and wherein the correction unit is operable to provide respective corrected temperature values for each of the plurality of thermocouples, in dependence upon respective determined temperature values and correction values for each of the plurality of thermocouples, and wherein the controller is operable to control the microwave energy supplied to the antenna in dependence upon the corrected temperature values for the plurality of thermocouples.

15. The apparatus as claimed in claim 9, wherein the controller is operable to terminate supply of the microwave energy from the power source when the corrected temperature value substantially reaches the predetermined target value.

* * * * *